(12) United States Patent
Reevell

(10) Patent No.: US 11,045,615 B2
(45) Date of Patent: Jun. 29, 2021

(54) VAPOR-GENERATING SYSTEMS

(71) Applicant: Altria Client Services LLC, Richmond, VA (US)

(72) Inventor: Tony Reevell, London (GB)

(73) Assignee: Altria Client Services LLC, Richmond, VA (US)

(*) Notice: Subject to any disclaimer, the term of this patent is extended or adjusted under 35 U.S.C. 154(b) by 305 days.

(21) Appl. No.: 15/846,610

(22) Filed: Dec. 19, 2017

(65) Prior Publication Data

US 2018/0169355 A1 Jun. 21, 2018

Related U.S. Application Data

(63) Continuation of application No. PCT/EP2017/082276, filed on Dec. 11, 2017.

(30) Foreign Application Priority Data

Dec. 19, 2016 (EP) .................................... 16205118

(51) Int. Cl.
*A61M 15/00* (2006.01)
*A61M 15/06* (2006.01)
(Continued)

(52) U.S. Cl.
CPC ....... *A61M 15/0036* (2014.02); *A24F 47/008* (2013.01); *A61M 11/042* (2014.02);
(Continued)

(58) Field of Classification Search
CPC .............. A61M 15/0036; A61M 15/06; A61M 11/042; A61M 2205/123; A24F 47/008
(Continued)

(56) References Cited

U.S. PATENT DOCUMENTS

2009/0095311 A1* 4/2009 Han ...................... A24F 47/002
131/194
2011/0226236 A1 9/2011 Buchberger
(Continued)

FOREIGN PATENT DOCUMENTS

CN 2018-78765 U * 6/2011 ........... A24F 47/008
EP 3104724 A1 12/2016
(Continued)

OTHER PUBLICATIONS

Extended European Search Report for European Patent Application No. 16205118 dated Jun. 14, 2017.
(Continued)

*Primary Examiner* — Thien S Tran
(74) *Attorney, Agent, or Firm* — Harness, Dickey & Pierce, P.L.C.

(57) ABSTRACT

A vapor-generating system includes a cartridge, a vapor-generating device and a piercing element. The cartridge includes a cartridge housing configured to hold a solid vapor-forming substrate within the cartridge housing interior, a liquid storage housing configured to hold a liquid vapor-forming substrate within the liquid storage housing interior, and a frangible seal on the liquid storage housing. The vapor-generating device includes a device housing at least partially defining a cavity, an electric heater, and a power supply. The piercing element is configured to pierce the frangible seal of the cartridge to expose the liquid storage housing interior to be in fluid communication with the electric heater based on the vapor-generating device coupling with the cartridge such that the device housing at least partially receives the cartridge into the cavity. The electric heater is located externally from the piercing element.

16 Claims, 4 Drawing Sheets

Figure 1:
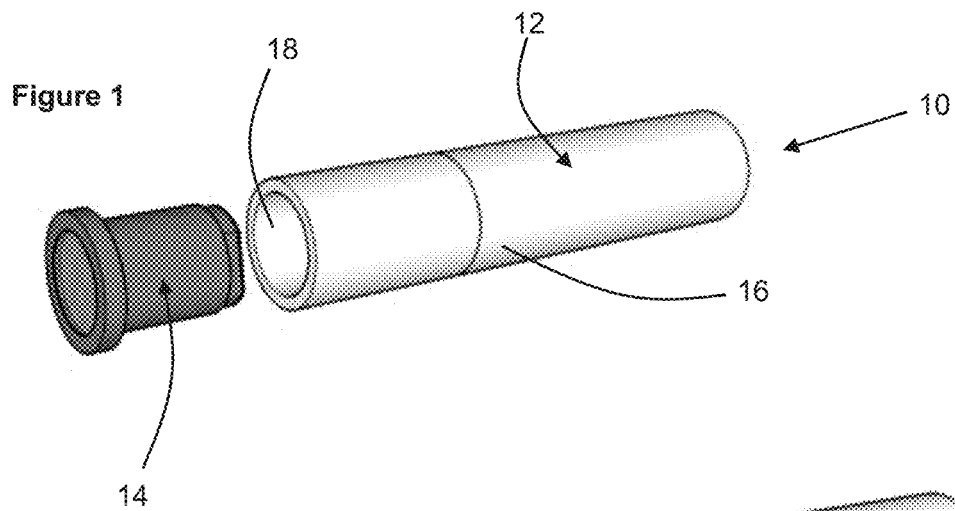

(51) Int. Cl.
*A24F 47/00* (2020.01)
*A61M 11/04* (2006.01)

(52) U.S. Cl.
CPC ...... *A61M 15/003* (2014.02); *A61M 15/0003* (2014.02); *A61M 15/06* (2013.01); *A61M 15/004* (2014.02); *A61M 2205/121* (2013.01); *A61M 2205/123* (2013.01); *A61M 2205/3653* (2013.01); *A61M 2205/8206* (2013.01)

(58) Field of Classification Search
USPC .................. 131/194, 207, 328, 329; 392/395
See application file for complete search history.

(56) References Cited

U.S. PATENT DOCUMENTS

| | | |
|---|---|---|
| 2013/0014772 A1 | 1/2013 | Liu |
| 2013/0333700 A1 | 12/2013 | Buchberger |
| 2015/0040929 A1* | 2/2015 | Hon ................... A24F 47/008 131/329 |
| 2015/0351456 A1 | 12/2015 | Johnson et al. |
| 2016/0227839 A1 | 8/2016 | Zuber et al. |
| 2016/0324215 A1* | 11/2016 | Mironov ................ B29C 43/14 |
| 2018/0297048 A1* | 10/2018 | Ricketts ............. B05B 11/0081 |

FOREIGN PATENT DOCUMENTS

| | | | | |
|---|---|---|---|---|
| RU | 2597531 C2 | 9/2016 | | |
| WO | WO-2015101479 A1 * | 7/2015 | ............. | A24B 15/16 |
| WO | WO-2015/179388 A1 | 11/2015 | | |
| WO | WO-2016/079151 A1 | 5/2016 | | |
| WO | WO-2016/116754 A1 | 7/2016 | | |
| WO | WO-2017001352 A2 * | 1/2017 | ......... | B05B 11/0081 |

OTHER PUBLICATIONS www.reuters.com/article/us-brit-am-tobacco-products-idUSKCN0T71U020151118<https://protect-us.mimecast.com/s/Jg6bBvC9X01ho> last accessed Dec. 18, 2017.
http://jinjiatech.com/PRODUCTS/Heat/91 <https://protect-us.mimecast.com/s/X8ygBguOLaRfM> last accessed Dec. 18, 2017.
International Preliminary Report on Patentability and Written Opinion thereof dated Jul. 4, 2019 for corresponding International Application No. PCT/EP2017/082276.
International Search Report and Written Opinion for PCT/EP2017/082276 dated Apr. 13, 2018.
Third Party Observation dated Mar. 26, 2020 for corresponding European Application No. 17816702.9.
Russian Office Action and Search Report dated Mar. 22, 2021 for corresponding Russian Application No. 2019120196, and English-language translation thereof.

* cited by examiner

VAPOR-GENERATING SYSTEMS

CROSS-REFERENCE TO RELATED APPLICATIONS

This application is a continuation of, and claims priority to, international application no. PCT/EP2017/082276, filed on Dec. 11, 2017, and further claims priority under 35 U.S.C. § 119 to European Patent Application No. 16205118.9, filed on Dec. 19, 2016, the entire contents of each of which are incorporated herein by reference.

BACKGROUND

Field

Some example embodiments relate to a vapor-generating system. The inventive concepts apply particularly to an electrically operated smoking ("vaping") system.

Description of Related Art

One type of vapor-generating system (also called an "aerosol-generating system") is an electrically operated vaping system. Known handheld electrically operated vaping systems typically comprise a vapor-generating device (also called an "aerosol-forming substrate") comprising a battery, control electronics and an electric heater for heating a vapor-forming substrate (also called an "aerosol-forming substrate"). The vapor-forming substrate may be contained within part of the vapor-generating device. For example, the vapor-generating device may comprise a liquid storage portion in which a liquid vapor-forming substrate, such as a nicotine solution, is stored. Such devices, often referred to as 'e-vapor devices', typically contain sufficient liquid vapor-forming substrate to provide a number of puffs (e.g., instances of generated vapor) equivalent to consuming multiple cigarettes. In an attempt to provide e-vapor device users ("adult vapers") with an experience that more closely simulates the experience of consuming a cigarette, some devices combine an e-vapor device configuration with a tobacco-based substrate to configure the devices to impart a tobacco flavor to the vapor generated by the devices. However, such devices may be impractically large and require the adult vaper to change a tobacco component and a liquid component at different times. It would be desirable to provide a vapor-generating system that mitigates or eliminates at least some of these problems with known devices.

SUMMARY

According to some example embodiments a aerosol-generating system may include a cartridge, a aerosol-generating device and a piercing element. The cartridge may include a cartridge housing at least partially defining a cartridge housing interior. The cartridge housing may be configured to hold a solid aerosol-forming substrate within the cartridge housing interior. The cartridge may include a liquid storage housing within the cartridge housing. The liquid storage housing may at least partially define a liquid storage housing interior. The liquid storage housing may be configured to hold a liquid aerosol-forming substrate within the liquid storage housing interior. The cartridge may include a frangible seal on the liquid storage housing. The aerosol-generating device may include a device housing at least partially defining a cavity, an electric heater, and a power supply. The aerosol-generating device may be configured to couple with the cartridge such that the device housing at least partially receives the cartridge into the cavity. The aerosol-generating device may be configured to supply power from the power supply to the electric heater. The piercing element may be configured to pierce the frangible seal of the cartridge to expose the liquid storage housing interior to be in fluid communication with the electric heater based on the device housing at least partially receiving the cartridge into the cavity. The electric heater may be located externally from the piercing element.

According to some example embodiments the piercing element may include a shaft portion, and a piercing portion at an end of the shaft portion.

According to some example embodiments the piercing portion may have a first end and a second end, the first end connected to the shaft portion and the second end opposite the first end, and the piercing portion may decrease in cross-sectional area in a direction from the first end to the second end.

According to some example embodiments the aerosol-generating device may include the piercing element.

According to some example embodiments the device housing may include a housing portion at least partially defining an end wall of the cavity, and the piercing element may extend from the end wall of the cavity into the cavity.

According to some example embodiments the electric heater may be on an outer surface of the piercing element.

According to some example embodiments the electric heater may include a resistive heating coil wound around a portion of the piercing element.

According to some example embodiments the piercing element may be a liquid transfer element configured to contact the liquid aerosol-forming substrate based on the device housing at least partially receiving the cartridge into the cavity.

According to some example embodiments the aerosol-generating device may include a base plate within the cavity, the electric heater may be on the base plate, and the piercing element may extend from the base plate into the cavity.

According to some example embodiments the aerosol-generating system may further comprise a liquid transfer element on the base plate and in contact with the electric heater. The liquid transfer element may be configured to contact the liquid aerosol-forming substrate based on the device housing at least partially receiving the cartridge into the cavity.

According to some example embodiments the cartridge may include the piercing element.

According to some example embodiments the piercing element may be configured to slide within the cartridge housing interior relative to the frangible seal.

According to some example embodiments the cartridge may include a base plate, and the piercing element may extend from the base plate into the cartridge housing interior.

According to some example embodiments the cartridge may further include a porous carrier material located externally from the liquid storage housing. The porous carrier material may be located adjacent the frangible seal.

According to some example embodiments a cartridge for a aerosol-generating system may include a cartridge housing, a liquid storage housing, and a frangible seal. The cartridge housing may at least partially define a cartridge housing interior. The cartridge housing may be configured to store a solid aerosol-forming substrate within the cartridge housing interior. The cartridge housing may be further configured to couple with a device housing of a aerosol-generating device such that at least a portion of the cartridge is inserted into a cavity at least partially defined by the device housing of the aerosol-generating device. The liquid storage housing may be within the cartridge housing. The liquid storage housing may at least partially define a liquid storage housing interior. The liquid storage housing may be configured to store a liquid aerosol-forming substrate within the liquid storage housing interior. The frangible seal may be on the liquid storage housing. The frangible seal may be configured to be pierced by a piercing element to expose the liquid storage housing interior to be in fluid communication with an electric heater of the aerosol-generating device based on the portion of the cartridge being inserted into the cavity.

According to some example embodiments the cartridge may further include the piercing element.

According to some example embodiments the piercing element may be configured to slide within the cartridge housing interior relative to the frangible seal.

According to some example embodiments the cartridge may further include a base plate, and the piercing element may extend from the base plate towards the cartridge housing interior.

According to some example embodiments the cartridge may further include a porous carrier material located externally from the liquid storage housing. The porous carrier material may be located adjacent the frangible seal.

BRIEF DESCRIPTION OF THE DRAWINGS

Example embodiments are further described, by way of example only, with reference to the accompanying drawings in which:

FIG. 1 shows a perspective view of a vapor-generating system according to some example embodiments of the inventive concepts and with the cartridge separate from the vapor-generating device;

FIG. 2 shows a perspective view of the vapor-generating system of FIG. 1 with the cartridge inserted into the vapor-generating device;

FIG. 3 shows a cross-sectional view of the vapor-generating system of FIG. 1 with the cartridge separate from the vapor-generating device;

FIG. 4 shows a cross-sectional view of the vapor-generating system of FIG. 1 with the cartridge inserted into the vapor-generating device;

FIG. 5 shows an exploded view of the cartridge of the vapor-generating system of FIG. 1;

FIG. 6 shows a cross-sectional view of a vapor-generating system according to some example embodiments of the inventive concepts and with the cartridge separate from the vapor-generating device;

FIG. 7 shows a cross-sectional view of the vapor-generating system of FIG. 6 with the cartridge inserted into the vapor-generating device;

FIG. 8 shows a cross-sectional view of a vapor-generating system according to some example embodiments of the inventive concepts and with the cartridge separate from the vapor-generating device; and FIG. 9 shows a cross-sectional view of the vapor-generating system of FIG. 8 with the cartridge inserted into the vapor-generating device.

DETAILED DESCRIPTION

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms “a”, “an” and “the” are intended to include the plural forms as well, unless the context clearly indicates otherwise. It will be further understood that the terms “comprises,” “comprising,” “includes,” and/or “including,” when used in this specification, specify the presence of stated features, integers, steps, operations, and/or elements, but do not preclude the presence or addition of one or more other features, integers, steps, operations, elements, and/or groups thereof.

It will be understood that when an element or layer is referred to as being “on”, “connected to” or “coupled to” another element or layer, it can be directly on, connected or coupled to the other element or layer or intervening elements or layers may be present. In contrast, when an element is referred to as being “directly on”, “directly connected to” or “directly coupled to” another element or layer, there are no intervening elements or layers present. As used herein, the term “and/or” includes any and all combinations of one or more of the associated listed items.

It will be understood that, although the terms first, second, etc. may be used herein to describe various elements, regions, layers and/or sections, these elements, regions, layers and/or sections should not be limited by these terms. These terms are only used to distinguish one element, region, layer or section from another region, layer or section. Thus, a first element, region, layer or section discussed below could be termed a second element, region, layer or section without departing from the teachings set forth herein.

Spatially relative terms, such as “beneath”, “below”, “lower”, “above”, “upper”, and the like, may be used herein for ease of description to describe one element or feature’s relationship to another element(s) or feature(s) as illustrated in the figures. It will be understood that the spatially relative terms are intended to encompass different orientations of the device in operation in addition to the orientation depicted in the figures. For example, if the device in the figures is turned over, elements described as “below” or “beneath” other elements or features would then be oriented “above” the other elements or features. Thus, the example term “below” can encompass both an orientation of above and below. The device may be otherwise oriented (rotated 90 degrees or at other orientations) and the spatially relative descriptors used herein interpreted accordingly.

Some example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

When the terms "about" or "substantially" are used in this specification in connection with a numerical value, it is intended that the associated numerical value include a tolerance of ±10% around the stated numerical value. The expression "up to" includes amounts of zero to the expressed upper limit and all values there between. When ranges are specified, the range includes all values there between such as increments of 0.1%. Moreover, when the words "generally" and "substantially" are used in connection with geometric shapes, it is intended that precision of the geometric shape is not required but that latitude for the shape is within the scope of the disclosure.

According to some example embodiments of the inventive concepts a vapor-generating system (also called an "aerosol-generating system") may include a cartridge, a vapor-generating device (also called an "aerosol-generating device") and a piercing element. The cartridge may include a cartridge housing, a solid vapor-forming substrate (also called a "solid aerosol-forming substrate") and a liquid vapor-forming substrate (also called a "liquid aerosol-forming substrate") each positioned within the cartridge housing, and a frangible seal. The vapor-generating device may include a device housing defining a cavity configured to receive the cartridge, an electric heater, a power supply and a controller configured to control a supply of electrical power from the power supply to the electric heater. The piercing element is configured to pierce the frangible seal when the cavity receives the cartridge. The electric heater is positioned externally from the piercing element.

As used herein, the term "vapor-forming substrate" (also called an "aerosol-forming substrate") is used to describe a substrate capable of releasing volatile compounds, which can form a vapor. The vapors generated from vapor-forming substrates of vapor-generating systems according to the inventive concepts may be visible or invisible and may include vapors (for example, fine particles of substances, which are in a gaseous state, that are ordinarily liquid or solid at room temperature) as well as gases and liquid droplets of condensed vapors.

Vapor-generating systems according to the some example embodiments may enable simultaneous replacement of a solid vapor-forming substrate and a liquid vapor-forming substrate by providing both substrates in a single cartridge. Advantageously, this may simplify use of the vapor-generating system for an adult vaper when compared to known devices in which a tobacco-based substrate and a nicotine solution may be replaced or replenished separately.

Providing a solid vapor-forming substrate and a liquid vapor-forming substrate in a single cartridge may simplify replenishment of the liquid vapor-forming substrate when compared to known devices in which an adult vaper may be required to refill a reservoir forming part of the device itself. Simplifying replenishment of the liquid vapor-forming substrate may advantageously enable a reduction in the amount of liquid vapor-forming substrate provided in the cartridge when compared to the amount of liquid vapor-forming substrate provided in known devices. Advantageously, this may allow vapor-generating systems according to the some example embodiments to be smaller than known devices.

Vapor-generating systems according to the some example embodiments provide an electric heater that is separate from the cartridge. Advantageously, this may reduce the cost and simplify the manufacture of the cartridge when compared to known devices in which a heater and a liquid vapor-forming substrate are combined into a single part ("element") of a vapor-generating device. Advantageously, providing an electric heater that is separate from the cartridge may enable cleaning of the electric heater, which may enable use of the electric heater with multiple cartridges. The electric heater may form an integral part of the vapor-generating device. The electric heater may be separable from the vapor-generating device, for example to enable cleaning or replacement of the electric heater.

Advantageously, providing the cartridge with a frangible seal may reduce or prevent the loss of volatile compounds from one or both of the solid vapor-forming substrate and the liquid vapor-forming substrate. Advantageously, the piercing element may automatically pierce the frangible seal when the cartridge is inserted into the cavity of the vapor-generating device for use.

The electric heater is positioned ("located") externally from the piercing element. That is, the electric heater is not positioned inside the piercing element. Advantageously, positioning the electric heater outside of the piercing element may enable cleaning of the electric heater.

In some example embodiments, the vapor-generating system may comprise at least one airflow inlet and at least one airflow outlet. During use, air flows through the vapor-generating system along a flow path from the airflow inlet to the airflow outlet. Air flows along the flow path from an upstream end of the flow path at the airflow inlet to a downstream end of the flow path at the airflow outlet. In some example embodiments, the vapor-generating system may be configured so that, in use, the solid vapor-generating substrate is positioned downstream of the liquid vapor-generating substrate.

The piercing element may have an elongate shape. The piercing element may comprise a hollow portion that defines an airflow passage through the piercing element. The piercing element may be solid.

The piercing element may comprise a shaft portion and a piercing portion at an end of the shaft portion. In some example embodiments in which the piercing element comprises a hollow portion, one or both of the piercing portion and the shaft portion may be hollow.

In some example embodiments, the piercing portion may have a first end connected to the shaft portion and a second end opposite the first end, wherein a cross-sectional area of the piercing portion decreases in size ("area") in a direction from the first end to the second end. In some example embodiments, the second end of the piercing portion may form a point. Advantageously, providing the second end of the piercing portion with a small cross-sectional area may reduce the force required to pierce the frangible seal.

The piercing element may form part of the vapor-generating device. The piercing element may extend from an end wall of the cavity, the piercing element extending into the cavity. Advantageously, providing the piercing element inside the cavity may reduce the risk of an adult vaper contacting the piercing element.

The electric heater may be provided ("located") on an outer surface of the piercing element. Advantageously, the piercing element may support the electric heater. The electric heater may comprise a resistive heating coil wound around a portion of the piercing element. In some example embodiments in which the piercing element comprises a shaft portion and a piercing portion, the resistive heating coil may be wound around part of the shaft portion.

The vapor-generating device may comprise a liquid transfer element. The liquid transfer element is configured to contact the liquid vapor-forming substrate when the cartridge is received within the cavity. The liquid transfer element may be configured to contact the liquid vapor-forming substrate based on the device housing at least partially receiving the cartridge into the cavity. The liquid transfer element may enable contact between the liquid vapor-forming substrate and the electric heater during use. In some example embodiments, the liquid transfer element may be positioned in direct contact with the electric heater.

The liquid transfer element may form ("comprise") the piercing element.

In some example embodiments in which vapor-generating device includes the piercing element, the liquid transfer element may be provided adjacent the piercing element. The piercing element may extend through the liquid transfer element.

The vapor-generating device may comprise a base plate positioned within the cavity, wherein the electric heater is positioned on the base plate and wherein the piercing element extends from the base plate. The piercing element may extend from the base plate into the cavity. The base plate may be formed integrally with the piercing element.

The piercing element may extend from a first side of the base plate. The electric heater may be positioned on a second side of the base plate. In some example embodiments, the base plate may comprise at least one aperture for the transfer of liquid vapor-forming substrate through the base plate when the cartridge is received within the cavity. In some example embodiments in which the vapor-generating device comprises a liquid transfer element, the liquid transfer element may be positioned on the base plate. The liquid transfer element may be positioned on the first side of the base plate. The piercing element may extend through the liquid transfer element.

The piercing element may form part of the cartridge. The piercing element may be configured to slide within the cartridge relative to the frangible seal when the cavity receives the cartridge. The piercing element may be configured to slide within the cartridge housing interior relative to the frangible seal. The cartridge may comprise a base plate and the piercing element extending from the base plate toward a cartridge interior. The base plate may be formed integrally with the piercing element. In some example embodiments, the base plate may comprise at least one aperture for the transfer of liquid vapor-forming substrate through the base plate when the cartridge is received within the cavity. In some example embodiments, the vapor-generating system may be configured so that part of the vapor-generating device acts upon the base plate when the cavity receives the cartridge. The vapor-generating system may be configured so that the electric heater acts upon the base plate when the cavity receives the cartridge. In some example embodiments in which the vapor-generating device comprises a liquid transfer element, the vapor-generating system may be configured so that the liquid transfer element acts upon the base plate when the cavity receives the cartridge.

In some example embodiments, the cartridge may comprise a liquid storage housing positioned within the cartridge housing, wherein the liquid vapor-forming substrate is positioned within the liquid storage housing and wherein the frangible seal is provided on the liquid storage housing. In some example embodiments, the frangible seal may be provided on an upstream end of the liquid storage housing.

In some example embodiments, the liquid storage housing may be retained within the cartridge housing by an interference fit.

In some example embodiments, an outer surface of the liquid storage housing may be shaped to define an airflow channel between the cartridge housing and the liquid storage housing when the liquid storage housing is received within the cartridge housing. The outer surface of the liquid storage housing may comprise a groove to define the airflow channel when the liquid storage housing is received within the cartridge housing.

The liquid storage housing may be tubular. The tubular liquid storage housing may have an open upstream end and a closed downstream end. In some example embodiments, the frangible seal may extend across the open upstream end.

The cartridge may comprise a porous carrier material positioned ("located") externally from the liquid storage housing and located adjacent the frangible seal. Advantageously, the liquid vapor-forming substrate may be absorbed into the porous carrier material when the piercing element pierces the frangible seal. Advantageously, the porous carrier material may substantially prevent liquid vapor-forming substrate leaking from the vapor-generating system when the piercing element pierces the frangible seal.

The porous carrier material may be retained in the cartridge housing by an interference fit. The porous carrier material may be provided in a porous carrier material housing, wherein the porous carrier material housing is retained in the cartridge housing by an interference fit.

The porous carrier material may be attached to the upstream end of the liquid storage housing.

In some example embodiments, in which the cartridge includes the piercing element, the piercing element may extend through the porous carrier material. In some example embodiments in which cartridge comprises a base plate, the porous carrier material may be positioned between the base plate and the liquid storage housing.

In some example embodiments in which the vapor-generating device comprises a liquid transfer element, the vapor-generating system may be configured so that the liquid transfer element contacts the porous carrier material when the cartridge is received within the cavity.

The porous carrier material may have an annular shape defining a passage through the porous carrier material. In some example embodiments, the vapor-generating system is configured so that the piercing element extends through the passage when the cartridge is received within the cavity. This may be particularly advantageous in some example embodiments in which the vapor-generating device comprises a liquid transfer element that forms the piercing element. Providing a passage extending through the porous carrier material may reduce the force required to push the piercing element through the porous carrier material.

The vapor-generating system may be configured so that the porous carrier material is compressed when the cavity receives the cartridge. In some example embodiments in which the vapor-generating system comprises a base plate, the base plate may exert a force on the porous carrier material when the cartridge is received within the cavity.

The cartridge may comprise an airflow channel positioned between the porous carrier material and the cartridge housing. In some example embodiments in which the porous carrier material is provided in a porous carrier material housing, the airflow channel may be positioned between the porous carrier material housing and the cartridge housing.

The porous carrier material may comprise any suitable material or combination of materials which is permeable to the liquid vapor-forming substrate and allows the liquid vapor-forming substrate to migrate through the porous carrier material. In some example embodiments, the material or combination of materials may be inert with respect to the liquid vapor-forming substrate. The porous carrier material may or may not be a capillary material. The porous carrier material may comprise a hydrophilic material to improve distribution and spread of the liquid vapor-forming substrate. This may assist with consistent vapor formation. The particular preferred material or materials will depend on the physical properties of the liquid vapor-forming substrate. Examples of suitable materials are a capillary material, for example a sponge or foam material, ceramic- or graphite-based materials in the form of fibers or sintered powders, a foamed metal or plastics material, a fibrous material, for example made of spun or extruded fibers, such as cellulose acetate, polyester, or bonded polyolefin, polyethylene, terylene or polypropylene fibers, nylon fibers or ceramic. The porous carrier material may have any suitable porosity so as to be used with different liquid physical properties.

In some example embodiments in which the vapor-generating device comprises a liquid transfer element, the liquid transfer element may comprise any suitable material or combination of materials which is able to convey the liquid vapor-forming substrate along its length. The liquid transfer element may be formed from a porous material, but this need not be the case. The liquid transfer element may be formed from a material having a fibrous or spongy structure. The liquid transfer element in some example embodiments may comprise a bundle of capillaries. For example, the liquid transfer element may comprise a plurality of fibers or threads or other fine bore tubes. The liquid transfer element may comprise sponge-like or foam-like material. In some example embodiments, the structure of the liquid transfer element may form ("comprise") a plurality of small bores or tubes, through which the liquid vapor-forming substrate can be transported by capillary action. The particular preferred material or materials will depend on the physical properties of the liquid vapor-forming substrate. Examples of suitable capillary materials include a sponge or foam material, ceramic- or graphite-based materials in the form of fibers or sintered powders, foamed metal or plastics material, a fibrous material, for example made of ("comprise") spun or extruded fibers, such as cellulose acetate, polyester, or bonded polyolefin, polyethylene, terylene or polypropylene fibers, nylon fibers, ceramic, glass fibers, silica glass fibers, carbon fibers, metallic fibers of medical grade stainless steel alloys such as austenitic 316 stainless steel and martensitic 440 and 420 stainless steels. The liquid transfer element may have any suitable capillarity so as to be used with different liquid physical properties. The liquid vapor-forming substrate has physical properties, including but not limited to viscosity, surface tension, density, thermal conductivity, boiling point and vapor pressure, which allow the liquid vapor-forming substrate to be transported through the liquid transfer element. The liquid transfer element may be formed from ("may comprise") heat-resistant material. The liquid transfer element may comprise a plurality of fibers strands. The plurality of fibers strands may be generally aligned along a length of the liquid transfer element.

In some example embodiments in which the vapor-generating system comprises a porous carrier material and a liquid transfer element, the porous carrier material and the liquid transfer element may comprise the same material. In some example embodiments, the porous carrier material and the liquid transfer element may comprise different materials.

The piercing element may be formed from any suitable material. In some example embodiments in which a liquid transfer element forms the piercing element, the piercing element may be formed from any suitable material described herein with respect to the liquid transfer element.

The piercing element may be formed from a metal. The piercing element may be formed from a plastic. Suitable materials include, but are not limited to, aluminum, stainless steel, polyether ether ketone (PEEK), polyimides, such as Kapton®, polyethylene terephthalate (PET), polyethylene (PE), high-density polyethylene (HDPE), polypropylene (PP), polystyrene (PS), fluorinated ethylene propylene (FEP), polytetrafluoroethylene (PTFE), polyoxymethylene (POM), epoxy resins, polyurethane resins, vinyl resins, liquid crystal polymers (LCP) and modified LCPs, such as LCPs with graphite or glass fibers.

The frangible seal may extend across an opening defined by the cartridge housing or, where present, the liquid storage housing. The frangible seal may extend across an end of the cartridge housing or an end of the liquid storage housing. The frangible seal may be secured to the cartridge housing or the liquid storage housing about a periphery of the frangible seal. The frangible seal may be secured to the cartridge housing or the liquid storage housing by at least one of an adhesive and a weld, such as an ultrasonic weld. The frangible seal is in some example embodiments formed from a sheet material. The sheet material may comprise at least one of a polymeric film and a metallic foil.

The electric heater may comprise a resistive heating coil. The pitch of the coil is in some example embodiments between about 0.5 millimeters and about 1.5 millimeters. In some Example embodiments the pitch of the coil is about 1.5 millimeters. The pitch of the coil means the spacing between adjacent turns of the coil. The coil may comprise fewer than six turns. In some example embodiments the coil may comprise fewer than five turns. The coil may be formed from (e.g., may comprise) an electrically resistive wire having a diameter of between about 0.10 millimeters and about 0.15 millimeters. In some example embodiments the coil may be formed from an electrically resistive wire having a diameter of about 0.125 millimeters. The electrically resistive wire is in some example embodiments formed of 904 or 301 stainless steel. Examples of other suitable metals include titanium, zirconium, tantalum and metals from the platinum group. Examples of other suitable metal alloys include, Constantan, nickel-, cobalt-, chromium-, aluminum-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminum based alloys and iron-manganese-aluminum based alloys. The resistive heating coil may also comprise a metal foil, such as an aluminum foil, which is provided in the form of a ribbon.

The electric heater may comprise a resistive heating mesh. A resistive heating mesh may be advantageous in some example embodiments in which the electric heater is provided on a base plate.

The resistive heating mesh may comprise a plurality of electrically conductive filaments. The electrically conductive filaments may be substantially flat. As used herein, "substantially flat" means formed in a single plane and not wrapped around or otherwise conformed to fit a curved or other non-planar shape. A flat heating mesh can be easily handled during manufacture and provides for a robust construction.

The electrically conductive filaments may define interstices between the filaments and the interstices may have a width of between about 10 micrometers and about 100 micrometers. In some example embodiments the filaments may give rise to capillary action in the interstices, so that in use, liquid vapor-forming substrate is drawn into the interstices, increasing the contact area between the heater assembly and the liquid.

The electrically conductive filaments may form a mesh of size between about 160 Mesh US and about 600 Mesh US (+/−10%) (that is, between about 160 and about 600 filaments per inch (+/−10%)). The width of the interstices may be between about 75 micrometers and about 25 micrometers. The percentage of open area of the mesh, which is the ratio of the area of the interstices to the total area of the mesh, is in some example embodiments between about 25 percent and about 56 percent. The mesh may be formed using different types of weave or lattice structures. The electrically conductive filaments may be an array of filaments arranged parallel to one another.

The electrically conductive filaments may have a diameter of between about 8 micrometers and about 100 micrometers. In some example embodiments the between about 8 micrometers and about 50 micrometers. In other example embodiments electrically conductive filaments may have a diameter between about 8 micrometers and about 39 micrometers.

The resistive heating mesh may cover an area of less than or equal to about 25 square millimeters. The resistive heating mesh may be rectangular. The resistive heating mesh may be square. The resistive heating mesh may have dimensions of about 5 millimeters by about 2 millimeters.

The electrically conductive filaments may comprise any suitable electrically conductive material. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminum-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminum based alloys and iron-manganese-aluminum based alloys. Timetal® is a registered trade mark of Titanium Metals Corporation. The filaments may be coated with one or more insulators. In some example embodiments the materials for the electrically conductive filaments are 304, 316, 304L, and 316L stainless steel, and graphite.

The electrical resistance of the resistive heating mesh is, in some example embodiments, between about 0.3 and about 4 Ohms. In some example embodiments the electrical resistance of the mesh may be between about 0.5 and about 3 Ohms. In other example embodiments the electrical resistance of the mesh may be about 1 Ohm.

The cartridge housing is, in some example embodiments, tubular and may include an upstream end and a downstream end. In some example embodiments, the solid vapor-forming substrate may be positioned within the downstream end. In some example embodiments, the liquid vapor-forming substrate may be positioned within the upstream end. Where present, the liquid storage housing and the porous carrier material may be located within the upstream end of the cartridge housing.

The solid vapor-forming substrate may be retained in the cartridge housing by an interference fit.

The cartridge may comprise a filter positioned downstream of the solid vapor-forming substrate. The filter may comprise a plug of filter material positioned within the downstream end of the cartridge housing. The plug of filter material may be retained within the cartridge housing by an interference fit. The filter may comprise a sheet material extending across a downstream opening of the cartridge housing. The sheet material may comprise a mesh. The sheet material may be secured to the cartridge housing by at least one of an adhesive and a weld, such as an ultrasonic weld. The filter may retain the solid vapor-forming substrate in the cartridge housing.

The vapor-generating system may comprise a mouthpiece ("outlet assembly"). In some example embodiments in which the vapor-generating system comprises at least one airflow outlet, the outlet assembly may include the at least one airflow outlet. The outlet assembly may form ("comprise") part of the cartridge. The outlet assembly may form part of the vapor-generating device. The outlet assembly may be formed separately from the cartridge and the vapor-generating device, wherein at least one of the cartridge and the vapor-generating device is configured to receive ("engage with," "couple with," etc.) the outlet assembly.

The solid vapor-forming substrate may comprise tobacco. The solid vapor-forming substrate may comprise a tobacco-containing material (also called a "tobacco material") containing volatile tobacco flavor compounds which are released from the substrate upon heating.

In some example embodiments, a tobacco material may include material from any member of the genus *Nicotiana*. In some example embodiments, the tobacco material includes a blend of two or more different tobacco varieties. Examples of suitable types of tobacco materials that may be used include, but are not limited to, flue-cured tobacco, Burley tobacco, Maryland tobacco, Oriental tobacco, rare tobacco, specialty tobacco, dark tobacco, blends thereof and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass.

The solid vapor-forming substrate may comprise tobacco containing deprotonated nicotine. Deprotonating the nicotine within tobacco may advantageously increase the volatility of the nicotine. Nicotine may be deprotonated by subjecting the tobacco to an alkalizing treatment.

The solid vapor-forming substrate may comprise a non-tobacco material. The solid vapor-forming substrate may comprise tobacco-containing material and non-tobacco containing material.

The solid vapor-forming substrate may include at least one vapor-former. As used herein, the term 'vapor former' (also called 'aerosol former') is used to describe any suitable known compound or mixture of compounds that, in use, enables formation of a vapor. Suitable vapor-formers include, but are not limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate.

Vapor formers may be polyhydric alcohols or mixtures thereof, such as propylene glycol, triethylene glycol, 1,3-butanediol and, most preferred, glycerine.

The solid vapor-forming substrate may comprise a single vapor former. In some example embodiments, the solid vapor-forming substrate may comprise a combination of two or more vapor formers.

The solid vapor-forming substrate may have a vapor former content of greater than 5 percent on a dry weight basis.

The solid vapor-forming substrate may have a vapor former content of between approximately 5 percent and approximately 30 percent on a dry weight basis.

The solid vapor-forming substrate may have a vapor former content of approximately 20 percent on a dry weight basis.

The liquid vapor-forming substrate may comprise a tobacco-containing material comprising volatile tobacco flavor compounds which are released from the liquid upon heating. The liquid vapor-forming substrate may comprise a non-tobacco material. The liquid vapor-forming substrate may include water, solvents, ethanol, plant extracts and natural or artificial flavors. In some example embodiments, the liquid vapor-forming substrate may comprise a vapor former. Suitable vapor formers include polyhydric alcohols or mixtures thereof, such as propylene glycol, triethylene glycol, 1,3-butanediol and glycerine.

The liquid vapor-forming substrate may comprise nicotine.

The liquid vapor-forming substrate may be free from nicotine. In such embodiments, the vaporized liquid vapor-forming substrate may be drawn through the solid vapor-forming substrate during use to strip one or more volatile compounds from the solid vapor-forming substrate. The vaporized liquid vapor-forming substrate may strip nicotine from the solid-vapor-forming substrate. A solid vapor-forming substrate comprising tobacco containing deprotonated nicotine may be particularly suited to embodiments in which the liquid vapor-forming substrate is free from nicotine.

At least one of the solid vapor-forming substrate and the liquid vapor-forming substrate may comprise a flavorant. The flavorant may include menthol.

The power supply may comprise a battery. For example, the power supply may be a nickel-metal hydride battery, a nickel cadmium battery, or a lithium based battery, for example a lithium-cobalt, a lithium-iron-phosphate or a lithium-polymer battery. The power supply may, in some example embodiments, be another form of charge storage device such as a capacitor. The power supply may require recharging and may have a capacity that allows for the storage of enough energy for use of the vapor-generating device with more than one cartridge.

Figure 2:
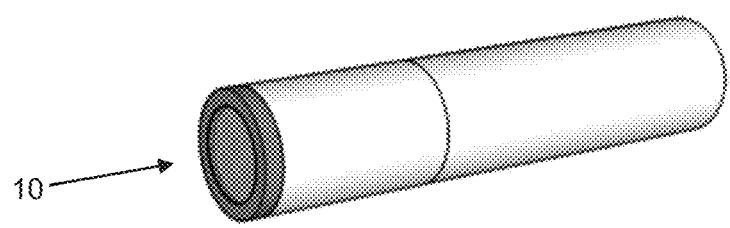
Figure 4:
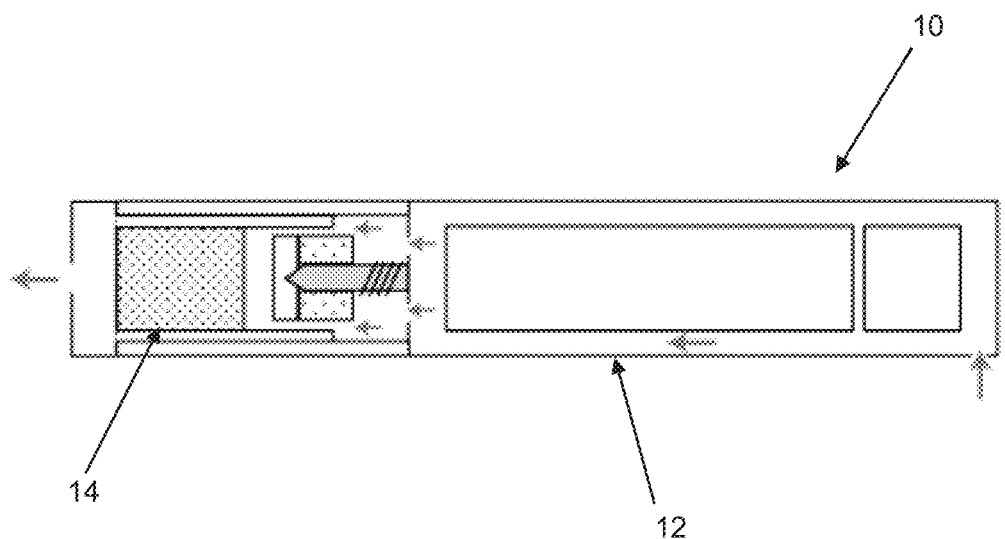

FIGS. 1 and 2 show a vapor-generating system 10 according to some example embodiments of the inventive concepts. The vapor-generating system 10 includes a vapor-generating device 12 and a cartridge 14. The vapor-generating device 12 may comprise a device housing 16 at least partially defining a cavity 18, where the cavity 18 is configured to receive an upstream end of the cartridge 14, for example as shown in FIGS. 2 and 4. Restated, the vapor-generating device 12 and the cartridge 14 are each configured to be coupled with each other, such that at least a portion of the cartridge 14 is inserted into the cavity 18 (restated, the device housing 16 at least partially receives the cartridge 14 into the cavity 18, the cartridge 14 is at least partially received into the cavity 18, etc.) and thus the cartridge 14, coupled to the vapor-generating device 12, is at least partially encompassed by the device housing 16 within the cavity 18. FIG. 1 shows the cartridge 14 separate from the vapor-generating device 12 and FIG. 2 shows the cartridge 14 coupled with the vapor-generating device 12 such that at least a portion of the cartridge 14 is received ("inserted") within the cavity 18 of the vapor-generating device 12.

Figure 3:
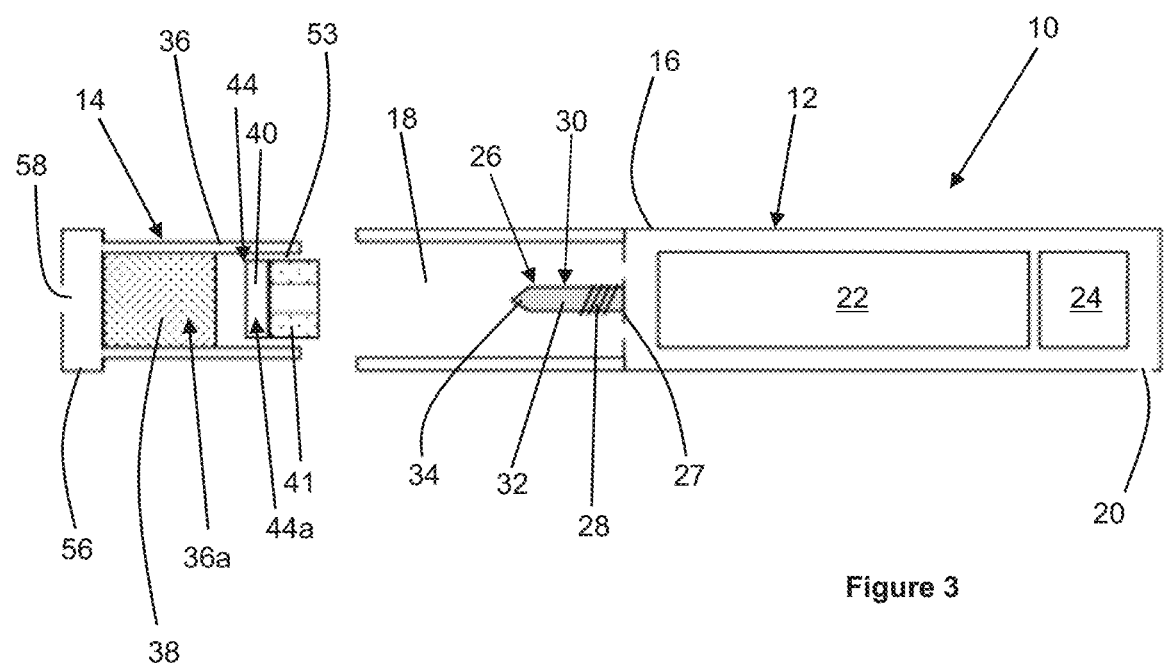

FIG. 3 shows a cross-sectional view of the vapor-generating system 10. The vapor-generating device 12 comprises an airflow inlet 20 positioned at an upstream end of the device housing 16. A power supply 22 and a controller 24 are positioned within the upstream end of the device housing 16. The vapor-generating device 12 may be configured to supply power from the power supply 22 to the electric heater 28 (e.g., based on operations performed by controller 24).

The vapor-generating system 10 further comprises a piercing element 26 and an electric heater 28 in the form of a resistive heating coil. The electric heater 28 may be positioned ("located") externally to the piercing element 26. During use, the controller 24 controls a supply of electrical power from the power supply 22 to the electric heater 28. The piercing element 26 extends from an upstream end wall 27 of the cavity 18 and comprises a shaft portion 32 and a piercing portion 34. As shown in at least FIGS. 3-4, the piercing portion 34 may have a first end connected to the shaft portion 32 and a second end opposite the first end, wherein a cross-sectional area of the piercing portion decreases in size ("cross-sectional area") in a direction from the first end to the second end. In some example embodiments, including the example embodiments shown in FIGS. 3-4, the second end of the piercing portion 34 may form a point. Advantageously, providing the second end of the piercing portion 34 with a small cross-sectional area may reduce the force required to pierce the frangible seal 48 by the piercing element 26. The device housing 16 may include a housing portion that at least partially defines the end wall 27 of the cavity 18. The piercing element 26 may extend from the end wall 27 of the cavity 18 into the cavity 18.

As shown in FIGS. 3-4, the electric heater 28 is positioned externally from the piercing element 26, such that the electric heater 28 is not located internally with regard to the piercing element 26 (e.g., the electric heater 28 is not within an interior of the piercing element 26). For example, as shown in FIGS. 3-4, the electric heater 28 may a resistive heating coil that is wrapped around a portion (e.g., the shaft portion 32) of the piercing element 26. The piercing element 26 also forms a liquid transfer element 30 and is formed from a material that enables transfer of liquid along the liquid transfer element 30 by capillary action.

Figure 5:
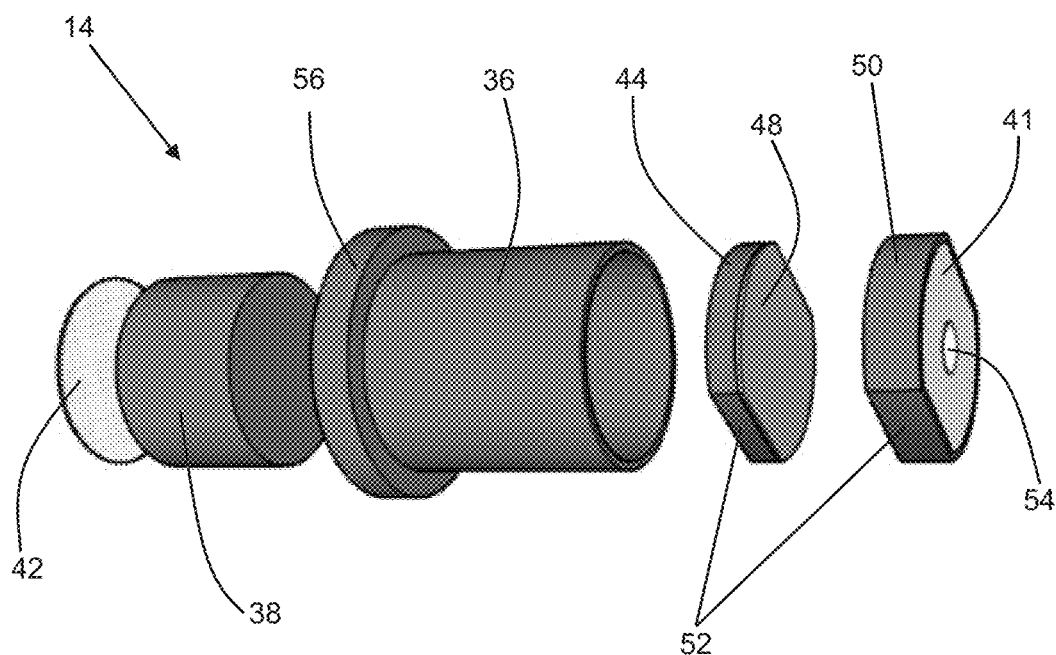

The cartridge 14 may comprise a cartridge housing 36, a solid vapor-forming substrate 38, a liquid vapor-forming substrate 40 and a porous carrier material 41 all positioned within the cartridge housing 36. FIG. 5 shows an exploded view of the cartridge 14. The cartridge housing 36 may at least partially define a cartridge housing interior 36a. The cartridge housing 36 may be configured to hold a solid vapor-forming substrate 38 within the cartridge housing interior 36a.

The cartridge 14 may include a cartridge housing 36, a liquid storage housing 44, and a frangible seal 48. The cartridge housing 36 may at least partially define a cartridge housing interior 36a, and the cartridge housing 36 may be configured to store a solid vapor-forming substrate 38 within the cartridge housing interior 36a. As shown in at least FIGS. 2 and 4, the cartridge housing 36 may be further configured to couple with the device housing 16 of the vapor-generating device 12 such that at least a portion of the cartridge 14 is inserted into a cavity 18 at least partially defined by the device housing 16 of the vapor-generating device 12. As shown in at least FIG. 3, the liquid storage housing 44 may be within the cartridge housing 36. The liquid storage housing 44 may at least partially define a liquid storage housing interior 44a. The liquid storage housing 44 may be configured to store a liquid vapor-forming substrate 40 within the liquid storage housing interior 44a. The frangible seal 48 may be on the liquid storage housing 44, and the frangible seal 48 may at least partially define the liquid storage housing interior 44a within which liquid vapor-forming substrate 40 may be held. The frangible seal 48 may be configured to be pierced by a piercing element 26 to expose the liquid storage housing interior 44a (e.g., expose the liquid storage housing interior 44a to be in fluid communication with an electric heater 28 of the vapor-generating device 12) based on the portion of the cartridge 14 being inserted into the cavity 18.

As described further below with reference to FIG. 4, the piercing element 26 may be configured to pierce the frangible seal 48 of the cartridge 14 to expose the liquid storage housing interior 44a to be in fluid communication with the electric heater 28 based on the device housing 16 at least partially receiving the cartridge 14 into the cavity 18. When the liquid storage housing interior 44a is thus exposed, the liquid vapor-forming substrate 40 may be released from the liquid forming housing interior 44a.

The solid vapor-forming substrate 38 comprises a tobacco plug positioned within the downstream end of the cartridge housing 36. A mesh filter 42 is attached to a downstream end of the cartridge housing 36 to retain the tobacco plug within the cartridge housing 36.

The liquid vapor-forming substrate 40 is contained within the liquid storage housing interior 44a that is at least partially defined by the liquid storage housing 44 retained within the upstream end of the cartridge housing 36 by an interference fit. The upstream end of the liquid storage housing 44 is open and the downstream end of the liquid storage housing 44 is closed. A frangible seal 48 extends across and is secured to the open upstream end of the liquid storage housing 44. Thus, the frangible seal 48 may at least partially define the liquid storage housing interior 44a.

The porous carrier material 41 is positioned within a porous carrier material housing 50 retained within the cartridge housing 36 by an interference fit. The porous carrier material 41 is positioned upstream of the liquid storage housing 44. The porous carrier material housing 50 is open at both ends so that the downstream end of the porous carrier material 41 contacts the frangible seal 48. Restated, the porous carrier material 41 is located externally from the liquid storage housing 44 and the porous carrier material 41 is located adjacent the frangible seal 48. The porous carrier material 41 has an annular shape and defines a passage 54 through the porous carrier material 41.

Planar side walls 52 of the liquid storage housing 44 and the porous carrier material housing 50 are spaced apart from the inner surface of the cartridge housing 36 to define an airflow passage 53 between the cartridge housing 36 and each of the liquid storage housing 44 and the porous carrier material housing 50.

The downstream end of the cartridge housing 36 forms an outlet assembly 56, the outlet assembly 56 defining an airflow outlet 58 of the vapor-generating system 10.

FIG. 4 shows a cross-sectional view of the vapor-generating system 10 after the cartridge 14 has been inserted into the cavity 18 of the vapor-generating device 12. As shown in FIGS. 2 and 4, the vapor-generating device 12 may be configured to couple with the cartridge 14 such that the device housing 16 at least partially receives the cartridge 14 into the cavity 18, also referred to herein as the cartridge 14 being inserted into the cavity 18. When the cartridge 14 is inserted into the cavity 18, the piercing element 26 may pierce the frangible seal 48 to thus expose the liquid storage housing interior 44a to be in fluid communication with the cavity 18, and thus with the electric heater 28. As a result of the liquid storage housing interior 44a being exposed to being in fluid communication with the cavity 18, liquid vapor-forming substrate 40 held in the liquid storage housing interior 44a may be released from the liquid storage housing interior 44a based on the piercing element 26 piercing the frangible seal 48. The piercing element 26 may be a liquid transfer element 30 configured to contact the liquid vapor-forming substrate 40 based on the device housing 16 at least partially receiving the cartridge 14 into the cavity 18 such that the piercing element 26 pierces the frangible seal 48. The liquid vapor-forming substrate released from the liquid storage housing interior 44a may be absorbed into the porous carrier material 41. The piercing element 26 also functions as a liquid transfer element 30, which is received within the passage 54 extending through the porous carrier material 41. The liquid transfer element 30 transfers liquid vapor-forming substrate 40 from the porous carrier material 41 to the electric heater 28 where the liquid vapor-forming substrate 40 is vaporized and then drawn out of the vapor-generating system 10 via airflow outlet 58. When an adult vaper draws on the outlet assembly 56, air is drawn into the vapor-generating system 10 through the airflow inlet 20, through the vapor-generating device 12 and into the cavity 18 where vaporized liquid vapor-forming substrate 40 is entrained in the airflow. The airflow then flows through the airflow passage 53 and through the solid vapor-forming substrate 38 where further volatile compounds are entrained in the airflow, and out through the airflow outlet 58.

Figure 6:
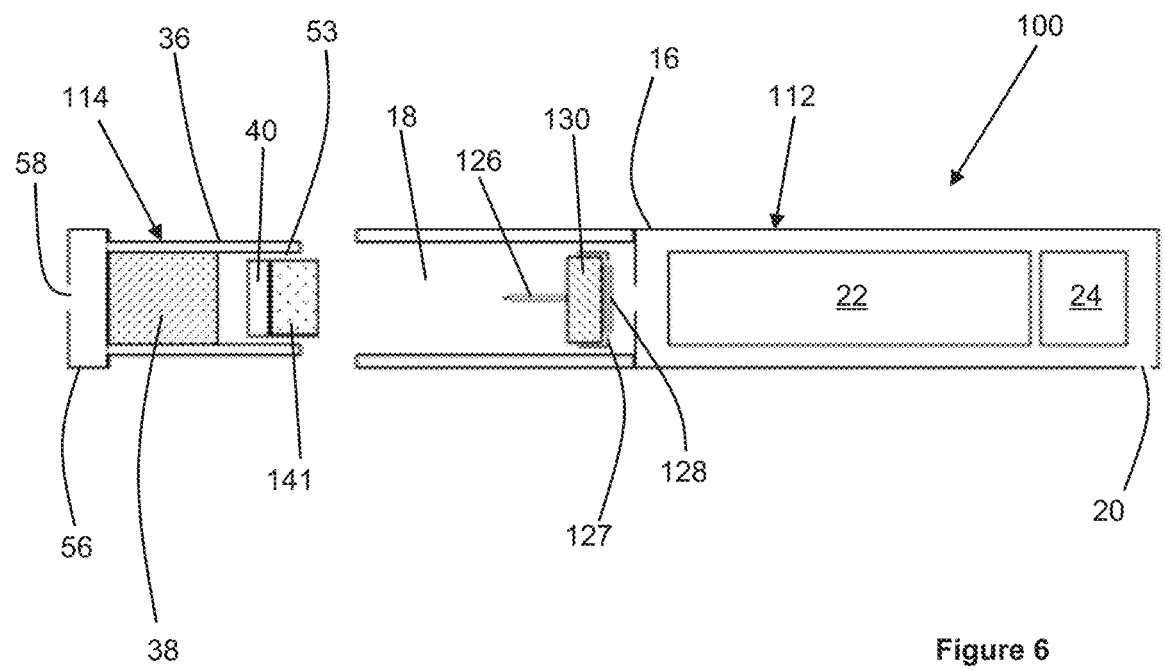
Figure 7:
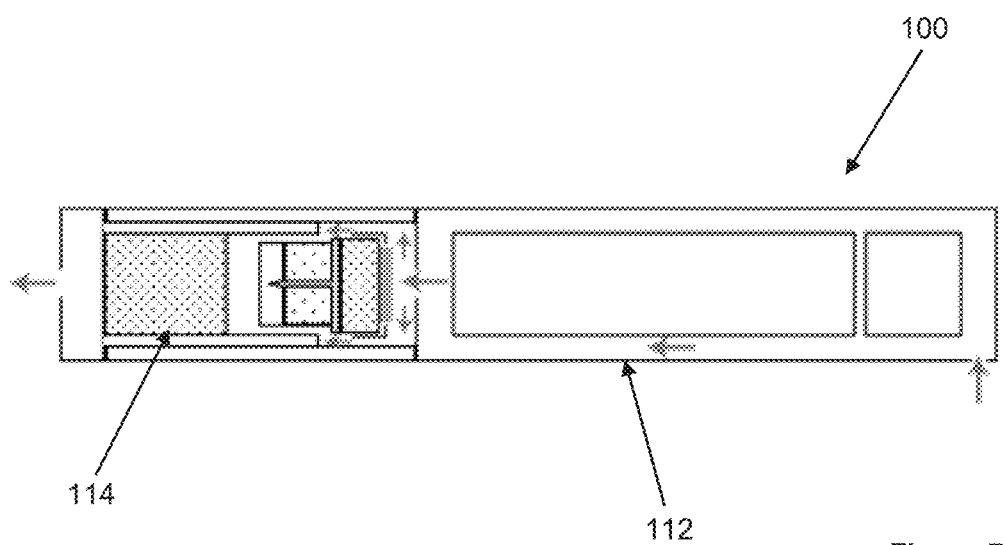

FIGS. 6 and 7 show a cross-sectional view of a vapor-generating system 100 according to some example embodiments of the inventive concepts. The vapor-generating system 100 is similar to the vapor-generating system 10 shown in FIGS. 1 to 5, and like reference numerals are used to designate like parts.

The vapor-generating system 100 comprises a cartridge 114 that is substantially the same as cartridge 14 described with reference to FIG. 5, except for the porous carrier material 141. In particular, the porous carrier material does not comprise a passage extending through the porous carrier material 141.

The vapor-generating system 100 comprises a vapor-generating device 112 that is similar to the vapor-generating device 12 shown in FIGS. 1 to 4. The vapor-generating device 112 comprises a base plate 127 mounted within the cavity 18 and a piercing element 126 extending from a first side of the base plate 127. A liquid transfer element 130 is also provided on the first side of the base plate 127 and thus is on the base plate, the piercing element 126 extending through the liquid transfer element 130. The piercing element 126 may extend from the base plate 127 into the cavity 18. An electric heater 128 in the form of a resistive mesh heater is positioned on a second side of the base plate 127 and thus is on the base plate 127. The base plate 127 comprises a plurality of aperture extending through the base plate 127 to provide fluid communication between the liquid transfer element 130 and the electric heater 128. The liquid transfer element 130 is in contact with the electric heater 128.

FIG. 7 shows the vapor-generating system 100 with the cartridge 114 inserted into the cavity 18 of the vapor-generating device 112. When the cartridge 114 is inserted into the cavity 18 the piercing element 126 pierces the frangible seal 48, which releases the liquid vapor-forming substrate 40 from the liquid storage housing 44. The liquid vapor-forming substrate 40 is then absorbed into the porous carrier material 141. The liquid transfer element 130 is configured to contact the liquid vapor-forming substrate 40 based on the device housing 16 at least partially receiving the cartridge 114 into the cavity 18. The liquid transfer element 130 contacts the upstream end of the porous carrier material 141 and transfers liquid vapor-forming substrate 40 from the porous carrier material 141 to the electric heater 28 where it is vaporized. The airflow through the vapor-generating system 100 is substantially the same as described herein with respect to the vapor-generating system 10 shown in FIG. 4.

Figure 8:
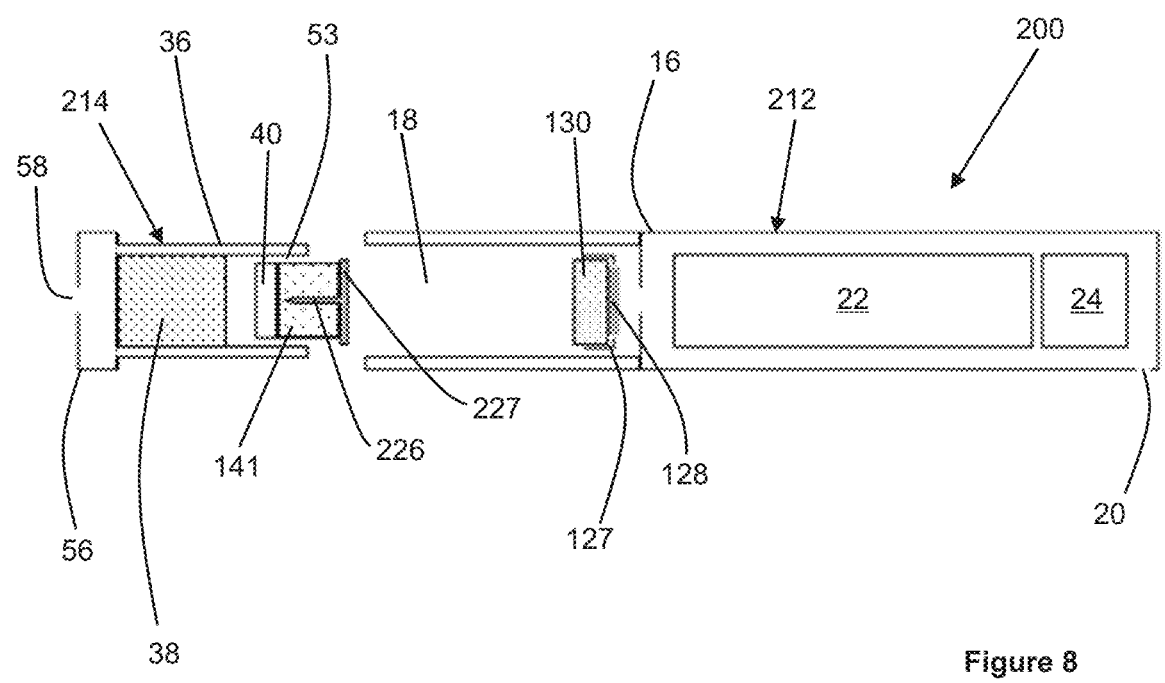
Figure 9:
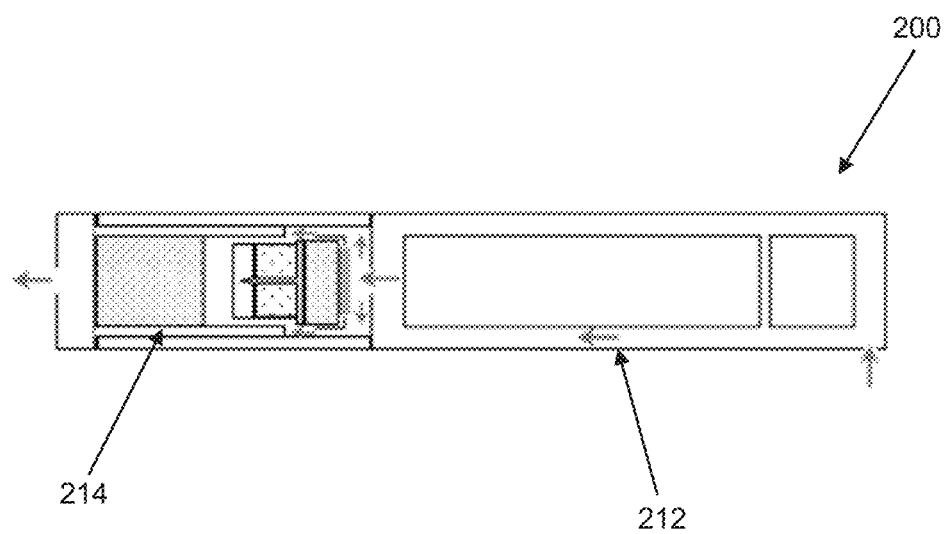

FIGS. 8 and 9 show a cross-sectional view of a vapor-generating system 200 according to some example embodiments of the inventive concepts. The vapor-generating system 200 is similar to the vapor-generating system 100 shown in FIGS. 6 and 7, and like reference numerals are used to designate like parts.

The vapor-generating system 200 differs by the position of the piercing element 226, which is provided in the cartridge 214 rather than the vapor-generating device 212. Restated, in some example embodiments, including the example embodiments shown in FIGS. 1-7, the vapor-generating device 12 may include the piercing element 26. In some example embodiments, including the example embodiments shown in FIGS. 8-9, the cartridge 214 may include the piercing element 226. Furthermore, as shown in FIGS. 8-9, the cartridge 214 may include a base plate 227 and a piercing element 226 that extends from the base plate 227 into the cartridge housing interior 36*a*. As shown in FIG. 8, the piercing element 226 is pre-inserted into the porous carrier material 141. Otherwise, the construction of the vapor-generating system 200 is the same as the construction of the vapor-generating system 100 shown in FIGS. 6 and 7.

FIG. 9 shows the vapor-generating system 200 with the cartridge 214 inserted into the cavity 18 of the vapor-generating device 212. The piercing element 226 may be configured to slide within the cartridge housing interior 36*a* relative to the frangible seal 48. When the cartridge 214 is inserted into the cavity 18 the liquid transfer element 130 exerts a force upon the piercing element 226. The force exerted on the piercing element 226 may slide the piercing element 226 within the porous carrier material housing 50 towards the frangible seal 48 until the piercing element 226 pierces the frangible seal 48. The operation of the vapor-generating system 200 is then identical to the operation of the vapor-generating system 100 of FIGS. 6 and 7.

The invention claimed is:

1. An aerosol-generating system comprising:
  a cartridge including,
    a cartridge housing at least partially defining a cartridge housing interior, the cartridge housing configured to hold a solid aerosol-forming substrate within the cartridge housing interior,
    a liquid storage housing within the cartridge housing, the liquid storage housing at least partially defining a liquid storage housing interior, the liquid storage housing configured to hold a liquid aerosol-forming substrate within the liquid storage housing interior, and
    a frangible seal on the liquid storage housing;
  an aerosol-generating device including,
    a device housing at least partially defining a cavity, the aerosol-generating device configured to couple with the cartridge such that the device housing at least partially receives the cartridge into the cavity,
    an electric heater, and
    a power supply, the aerosol-generating device configured to supply power from the power supply to the electric heater; and
  a piercing element configured to pierce the frangible seal of the cartridge to expose the liquid storage housing interior to be in fluid communication with the electric heater based on the device housing at least partially receiving the cartridge into the cavity,
  wherein the electric heater is located externally from the piercing element,
  wherein the cartridge further includes a porous carrier material located externally from the liquid storage housing, the porous carrier material located adjacent the frangible seal and contacting the frangible seal, and
  wherein the piercing element is configured to extend through either the porous carrier material or a passage extending through the porous carrier material to pierce the frangible seal, such that liquid vapor-forming substrate released from the liquid storage housing interior via the pierced frangible seal is absorbed into at least the porous carrier material.

2. The aerosol-generating system according claim 1, wherein
the piercing element includes
a shaft portion, and
a piercing portion at an end of the shaft portion.

3. The aerosol-generating system according to claim 2, wherein
the piercing portion has a first end and a second end, the first end connected to the shaft portion and the second end opposite the first end, and
the piercing portion decreases in cross-sectional area in a direction from the first end to the second end.

4. The aerosol-generating system according to claim 1, wherein the aerosol-generating device includes the piercing element.

5. The aerosol-generating system according to claim 4, wherein
the device housing includes a housing portion at least partially defining an end wall of the cavity,
the piercing element extends from the end wall of the cavity into the cavity, and
the porous carrier material has an annular shape that defines the passage extending through the porous carrier material, and the piercing element is configured to extend through the passage extending through the porous carrier material to pierce the frangible seal.

6. The aerosol-generating system according to claim 5, wherein
the electric heater is on an outer surface of the piercing element.

7. The aerosol-generating system according to claim 6, wherein the electric heater includes a resistive heating coil wound around a portion of the piercing element.

8. The aerosol-generating system according to claim 5, wherein the piercing element is a liquid transfer element configured to contact the liquid aerosol-forming substrate based on the device housing at least partially receiving the cartridge into the cavity and is configured to transfer liquid from the porous carrier material to the electric heater by capillary action, based on the piercing element extending through the passage of the porous carrier material to pierce the frangible seal.

9. The aerosol-generating system according to claim 4, wherein
the aerosol-generating device includes a base plate within the cavity,
the electric heater is on the base plate,
the piercing element extends from the base plate into the cavity, and
the porous carrier material does not include the passage extending through the porous carrier material, such that the piercing element is configured to extend through the porous carrier material to pierce the frangible seal.

10. The aerosol-generating system according to claim 9, further comprising:
a liquid transfer element on the base plate and in contact with the electric heater, the liquid transfer element configured to contact the porous carrier material based on the device housing at least partially receiving the cartridge into the cavity such that the piercing element extends through the porous carrier material to pierce the frangible seal.

11. The aerosol-generating system according to claim 1, wherein the cartridge includes a base plate and the piercing element extends from the base plate into the cartridge housing interior, and the porous carrier material does not include the passage extending through the porous carrier material, such that the piercing element is configured to extend through the porous carrier material to pierce the frangible seal.

12. The aerosol-generating system according to claim 11, wherein the piercing element is configured to slide within the cartridge housing interior relative to the frangible seal.

13. A cartridge for an aerosol-generating system, the cartridge comprising:
a cartridge housing at least partially defining a cartridge housing interior, the cartridge housing configured to store a solid aerosol-forming substrate within the cartridge housing interior, the cartridge housing further configured to couple with a device housing of an aerosol-generating device such that at least a portion of the cartridge is inserted into a cavity at least partially defined by the device housing of the aerosol-generating device,
a liquid storage housing within the cartridge housing, the liquid storage housing at least partially defining a liquid storage housing interior, the liquid storage housing configured to store a liquid aerosol-forming substrate within the liquid storage housing interior,
a frangible seal on the liquid storage housing, the frangible seal configured to be pierced by a piercing element to expose the liquid storage housing interior to be in fluid communication with an electric heater of the aerosol-generating device based on the portion of the cartridge being inserted into the cavity, and
a porous carrier material located externally from the liquid storage housing, the porous carrier material located adjacent the frangible seal, wherein
the porous carrier material has an annular shape defining a passage extending through the porous carrier material, the porous carrier material configured to direct the piercing element through the passage to pierce the frangible seal such that liquid vapor-forming substrate released from the liquid storage housing interior via the pierced frangible seal is absorbed into at least the porous carrier material, or
the porous carrier material does not include the passage extending through the porous carrier material, such that the piercing element is configured to extend through the porous carrier material to pierce the frangible seal such that liquid vapor-forming substrate released from the liquid storage housing interior via the pierced frangible seal is absorbed into at least the porous carrier material.

14. The cartridge according to claim 13, further comprising:
the piercing element, wherein the porous carrier material does not include the passage extending through the porous carrier material, such that the piercing element is configured to extend through the porous carrier material to pierce the frangible seal.

15. The cartridge according to claim 14, wherein the piercing element is configured to slide within the cartridge housing interior relative to the frangible seal.

16. The cartridge according to claim 15, further comprising:
a base plate, the piercing element extending from the base plate towards the cartridge housing interior and at least partially through the porous carrier material.

* * * * *